United States Patent [19]

Shinoda et al.

[11] Patent Number: 5,041,529

[45] Date of Patent: Aug. 20, 1991

[54] PREPARATION PROCESS FOR BIOABSORBABLE POLYESTER

[75] Inventors: Hosei Shinoda, Aichi; Masami Ohtaguro, Nagoya, both of Japan

[73] Assignee: Mitsui Toatsu Chemicals, Inc., Tokyo, Japan

[21] Appl. No.: 427,642

[22] Filed: Oct. 27, 1989

[30] Foreign Application Priority Data

Nov. 7, 1988 [JP] Japan ................................ 63-279466
Nov. 7, 1988 [JP] Japan ................................ 63-279467

[51] Int. Cl.$^5$ ........................ C08G 63/08; C08G 63/88
[52] U.S. Cl. .................................... 528/354; 528/481; 528/501
[58] Field of Search ........................ 528/354, 481, 501

[56] References Cited

U.S. PATENT DOCUMENTS

| | | | |
|---|---|---|---|
| 3,565,869 | 2/1971 | De Prospero | 528/359 X |
| 3,621,003 | 11/1971 | Selman et al. | 528/481 |
| 3,772,420 | 11/1973 | Glick et al. | 528/354 X |
| 3,890,283 | 6/1975 | Casey et al. | 528/481 X |
| 4,439,602 | 3/1984 | McCurdy et al. | 528/481 |
| 4,677,191 | 6/1987 | Tanaka et al. | 528/354 X |
| 4,728,721 | 3/1988 | Yamamoto et al. | 528/354 X |
| 4,797,468 | 1/1989 | De Vries | 528/354 |

*Primary Examiner*—Earl Nielsen
*Attorney, Agent, or Firm*—Burns, Doane, Swecker & Mathis

[57] ABSTRACT

The invention relates to a process for the preparation of a bioabsorbable polyester comprising reacting said polyester under reduced pressure in the reaction system while maintaining said polyester in the molten state during the second half of the polymerization reaction or after completion of the reaction and obtaining said polyester which contain almost no residue of unreacted monomers and volatile ingredients of low molecular weight.

15 Claims, No Drawings

PREPARATION PROCESS FOR BIOABSORBABLE POLYESTER

BACKGROUND OF THE INVENTION

1. Field of the Invention

The present invention relates to a process for the preparation of bioabsorbable polyester for use in medical devices such as surgical sutures, matrices for sustained release of drugs and internal splint-plates in fracture fixation. More particularly the invention relates to a process for preparing bioabsorbable polyesters, that is, a glycolic-acid based polymer, lactic-acid based polymer and glycolic-acid/lactic-acid based copolymer, which contain almost no residues of unreacted monomers or volatile ingredients of low molecular weight.

2. Prior Art of the Invention

Bioabsorbable polyesters having recurring structural units represented by the formula (I):

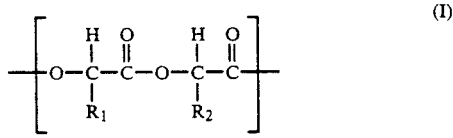

wherein $R_1$ and $R_2$ are a hydrogen atom or a methyl group and can be the same or different, are divided into a glycolic-acid based polymer wherein a 80 to 100% portion of $R_1$ and $R_2$ is a hydrogen atom and a 0 to 20% portion is a methyl group, and a lactic-acid based polymer wherein a 0 to 80% portion of $R_1$ and $R_2$ is a hydrogen atom and 20 to 100% portion is a methyl group.

The former glycolic-acid based polymer has hydrolyzability and bioabsorbability. High molecular weight polymers of glycolic acid may be processed into fibers and used for materials of sterile surgical treatment such as sutures and gauze. Surgical sutures of glycolic-acid based polymer have already been marketed from ACC Co. under the trade mark of Dexon (100% by mole of glycolic acid structure) and from Ethicon Co. under the trade mark of Vicril (from 85 to 90% by mole of glycolic acid structure and from 10 to 15% by mole of lactic acid structure).

The lactic-acid based polymer is an interesting bioabsorbable material which is nonenzymatically decomposed in vivo into glycolic acid and lactic acid. These acids are finally converted to carbon dioxide and water through a metabolic pathway and are excreted from the organism.

Lactic-acid/glycolic-acid copolymer and lactic acid homopolymer are particularly excellent in processability and solubility in various solvents. These polymers are hence processed into pellets, needles, films and microspheres, and employed for the matrix for sustained release of drugs for use in internal imbedding and intravenous injection. High molecular weight homopolymers of lactic acid may be particularly processed into bars or plates and the use for bioabsorbable plates of internal splint in fracture fixation is now under development.

A process for preparing the bioabsorbable polyesters has conventionally been known to carry out polymerization of glycolide or lactide in the presense of a catalyst such as trifluoro antimony or stannous chloride. The process, however, has caused problems due to the toxicity of the catalyst used. Accordingly, preparation processes for eliminating the toxicity problems of the catalyst have been proposed. For example, a process has also been known to use stannous octoate as the catalyst, which compound has been admitted as a nontoxic stabilizer by the Food and Drug Administration in USA [Polymer, Vol. 20, 14-59(1979)].

Since then various processes have been proposed for the preparation of bioabsorbable polyesters.

For example, the following processes have been proposed for the preparation of glycolic-acid based polymers. (1) Japanese Patent Publication No. 62-31736(1987) discloses a preparation process for polyglycolic acid comprising polymerizing glycolide at a temperature of 160° to 180° C. in the presence of stannous octoate in an amount from 0.01 to 0.05% by weight per weight of glycolide and a monohydric alcohol of saturated aliphatic straight chain containing even numbers of from 12 to 18 carbon atoms in an amount from 0.5 to 2.8 times by weight per weight of stannous octoate. (2) Japanese Patent Laid-Open No. 63-17927(1988) discloses a preparation process for polyglycolic acid having an inherent viscosity of 0.85 to 1.1dl/g comprising polymerizing glycolide at a temperature of 220° to 250° C. in the presence of stannous octoate in an amount from 0.001 to 0.005% by weight per weight of glycolide and a monohydric alcohol of aliphatic straight chain containing from 10 to 18 carbon atoms in an amount from 0.11 to 0.22% by mole per mole of glycolide.

On the other hand, processes have also been proposed for the preparation of lactic-acid based polymers. For example, Japanese Patent Laid-Open No. 62-64824(1987) discloses a low molecular weight heterogeneous lactic-acid/glycolic-acid copolymer containing from 25 to 100% by mole of lactic acid structure and from 0 to 75% by mole of glycolic acid structure and having an inherent viscosity of 4 dl/g or less in a 1g/100ml solution of chloroform or dioxane; and a preparation process for the copolymer. An example of the above-mentioned Japanese Patent Laid-Open No. 62-64824(1987) describes a process for conducting polymerization of lactide with glycolide at 160° C. by using 0.2% by weight of stannous octoate as a catalyst in the presence of dl-lactic acid to obtain the desired copolymer.

As described above, various processes have been known in the preparation of bioabsorbable polyesters. When these processes are used for the preparation of bioabsorbable polyesters, it is generally inevitable that from two to several percent of unreacted monomers, i.e., lactide and/or glycolide used as raw materials remains in the resultant polymer. Low molecular weight volatile substances such as impurities having relatively low-boiling points and chain or cyclic oligomers which were formed as by-products during the polymerization have also been known to remain in the resultant polymer.

According to information of the present inventors, glycolic-acid based polymers contain in some cases several percent of residual impurities such as unreacted glycolide and low molecular weight volatile substances. These residual impurities evaporate and generate bubbles in the polymer filament extruded from a nozzle in the spinning step of suture production from the glycolic-acid based polymer. Consequently, end breakage due to the bubbles frequently occurs in the spinning step. It has also been known that the filament obtained is unfavorable because the filament tends to cause fluctuations in strength and hydrolizability Lactic acid based polymer experience deterioration in storage stability and processability due to the unreacted glycolide and lactide and low molecular weight volatile substances remaining in the polymer. When the polymer is used for a matrix for sustained release of drugs, these impurities tend to make the internal release of drugs intermittent and are liable to cause an early burst phenomenon where a large amount of drugs are released in the initial period. When an internal splint-plate is molded using lactic-acid based polymers of high molecular weight, unreacted monomer and by-products remaining in a large amount lower the strength of the molded splint-plate.

Various problems are thus caused by unreacted monomers and low molecular weight volatile substances remaining in the bioabsorbable polyesters. However, a process for the preparation of bioabsorbable polyesters containing a small amount of these impurities has not yet been proposed.

Glycolic-acid based polymers of high molecular weight which are suitable for spinning are soluble in a few kinds of expensive solvents such as hexafluoroisopropanol(HFIP) and are insoluble in solvents generally used in the industry. Hence, it is industrially unfavorable to apply purification processes such as a reprecipitation method in order to reduce the content of the unreacted monomers and low molecular weight volatile substances. Accordingly, an extraction method can be considered which removes residual monomers by extracting with solvents such as ethyl acetate. The process, however, is also industrially disadvantageous because production steps are complex and problems are further found on removing the extraction solvents remaining in the polymer.

U.S. Pat. No. 3,565,869 discloses a method for removing monomers and low molecular weight volatile substances remaining in the polymer by contacting small pieces of polyglycolic acid with a high temperature inert gas. The present inventors, however, have investigated the process and have found that the process cannot effectively remove the volatile substances such as monomers because the polymer is solid. It takes more than several tens of hours to reduce the amount of residual monomer to the level of 2% or less. The polymer decomposes during the treatment and the molecular weight decreases.

Additionally, the above-mentioned Japanese Patent Laid-Open No.62-64824(1987) discloses a process for the purification of lactic-acid based polymer by reprecipitating the formed polymer after completing the polymerization.

In the process, the formed polymer is dissolved in a good solvent such as chloroform and poured into a poor solvent such as methanol to precipitate the insoluble polymer alone and to remove soluble monomers. The process, however, requires complex steps, lowers the yield of the polymer and is hence industrially unfavorable.

The polymer for use in the matrix for sustained release of drugs in order to continuously release medicine over a long period is desired to be polydisperse in the above-mentioned Japanese Patent Laid-Open No. 62-64824(1987). However, in the purification by the reprecipitation method, the polymer having a relatively low molecular weight is removed by dissolution in the solvent and thus the polymer obtained as insoluble matter has a narrow molecular weight distribution and impaired polydispersibility. Consequently, the polymer is unsuitable for use in the matrix.

The most serious disadvantage of the reprecipitation method is the organic solvent which inevitably remains in the polymer because the organic solvent is used for the purification in the reprecipitation method.

Consequently, the bioabsorbable polyesters purified by the reprecipitation method are difficult to use in medical care.

SUMMARY OF THE INVENTION

The object of this invention is to provide an improved process for the preparation of a bioabsorbable polyester in order to eliminate the above problems in the conventional preparation process for bioabsorbable polyesters.

More particularly, the object is to provide a process for preparing the bioabsorbable polyester containing a small amount of residual monomers and low molecular weight volatile substances. The polyester comprises a polyglycolic-acid based polymer for use in, for example, surgical sutures and drug matrices for sustained release and a polylactic-acid based polymer applied to drug matrices for sustained release and medical devices such as internal splint-plates used in fracture fixation.

The present inventors have carried out an intensive investigation on the above subjects. As a result, it has been found that, by maintaining the polymer at a specific temperature under a specific condition of reduced pressure in the course of or after completion of the polymerization reaction, residual monomers and low molecular weight volatile substances can be effectively removed without impairing the quality of the polymer. Thus, the present invention has been completed.

One aspect of this invention is a process for the preparation of a bioabsorbable polyester having recurring structural units represented by the formula (I) :

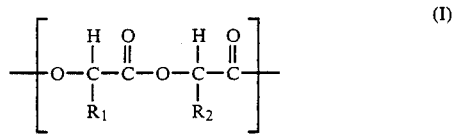

wherein $R_1$ and $R_2$ are a hydrogen atom or a methyl group and can be the same or different, by the polymerization reaction of a glycolide and/or a lactide which comprises treating said polyester under reduced pressure in the reaction system while maintaining said polyester in a molten state during the second half of the polymerization reaction or after completion of the reaction.

The present invention can be favorably carried out by reducing the pressure of the reaction system to 5 mm Hg or less, by reducing the pressure of the reaction system and simultaneously ventilating an inert gas through the polymer in a molten state, or by reducing the pressure of the reaction system to 5 mm Hg or less and simultaneously ventilating an inert gas through the polymer in a molten state.

In the case where the bioabsorbable polyester is a glycolic-acid based polymer wherein a 80 to 100% portion of $R_1$ and $R_2$ is a hydrogen atom and a 0 to 20% portion is a methyl group in the recurring structural units represented by the formula(I), the process of this invention can be preferably carried out by maintaining the reaction temperature in the range of from the melting point of said polymer to 250° C. over the second half of the reaction period. When the bioabsorbable polyester is a lactic-acid based polymer wherein a 0 to 80% portion of $R_1$ and $R_2$ is a hydrogen atom and a 20 to 100% portion is a methyl group in the recurring structural units represented by the formula (I), the process of this invention can be preferably carried out by maintaining the reaction temperature in the range of from the glass transition temperature of said polymer to 200° C. above the glass transition temperature over the second half of the reaction period.

The bioabsorbable polyester containing 2% or less in a residual amount of unreacted monomers and low molecular weight volatile substances can be prepared by these processes.

The present invention can prepare a bioabsorbable polyester containing only a small amount of unreacted monomers and low molecular weight volatile substances by carrying out a simple process.

Particularly, the glycolic-acid base polymer having an inherent vicosity of 0.9 dl/g or more and containing 2% or less of residual monomers and low molecular weight volatile substances can be prepared by a relatively simple process. Spinning and drawing can be smoothly carried out without end breakage by using the glycolic-acid based polymer thus obtained. A filament having a high strength can be obtained.

Further, the glycolic-acid based polymer contains only a small amount of residual monomers and low molecular weight substances, and hence is excellent in storage stability and also reduces fluctuations in hydrolyzability and retention of strength as an absorbable suture. These effects are very important for the polymer in view of the character of application.

In the bioabsorbable polyester of the glycolic-acid based polymer obtained by the process of this invention, the polymerization reaction system once passes through the molten state. Hence, the resulting polymer becomes homogeneous and stabilizaiton of spinning and drawing steps can be expected, which situation is industrially advantageous.

The bioabsorbable polyester of the lactic-acid based polymer obtained by the process of this invention contains only a small amount of residual monomers and hence is excellent in processability and storage stability. Further, in the case where the polymer is used for the matrix for sustained release of drugs, the polymer prevents the burst phenomenon which releases a large amount of medicine in the early stage of administration.

The polymer also has a broad molecular weight distribution and is polydisperse, and hence is particularly suitable for use as the matrix for sustained release of drugs which require continuous release of medicine over a long period.

The bioabsorbable polyester obtained by the process of this invention contains entirely no residue of organic solvents which are toxic to a human body. Consequently, no restriction is imposed upon the application of the polymer to medical care in view of no toxicity. The stuation is an important advantage of this invention.

DETAILED DESCRIPTION OF THE INVENTION

In the recurring structural units represented by the formula (I) of this invention, the lactic acid structure wherein $R_1$ and $R_2$ are methyl groups may be a L-isomer or a D-isomer. It is not required to be the L-isomer alone or D-isomer alone. Both isomers may also be mixed in arbitrary proportions.

In the process of this invention, the reaction product is maintained in a molten state over the second half of the polymerization reaction and at the same time gradually decreasing the pressure of the reaction system from atmospheric pressure and finally keeping the pressure at about 5 mm Hg or less. Thereby the bioabsorbable polyester can decrease the content of unreacted monomers and low molecular weight volatile substances to 2% or less.

In the process of this invention, the term "the second half of the polymerization reaction" means the period after the inherent viscosity of resulting polymer in the reaction has increased to 90% or more of the desired inherent viscosity. Consequently, the time for starting the operation of maintaining the product in the molten state and pressure reduction is suitably determined depending upon polymerization temperature, catalyst amount and amount of molecular weight regulator.

The operation for the glycolic-acid based polymer is preferably started after the inherent viscosity of the polymer has increased to 0.9dl/g or more. When the operation of maintaining the product in the molten state and pressure reduction is started before the inherent viscosity reaches to 0.9 dl/g, the polymer obtained after completing polymerization is incapable of or very difficult to melt-spin. Additionally, even though the polymer can be spun, the filament obtained is low in strength and unsuitable for use in sutures.

The inherent viscosity is measured with a Ubbelohde viscometer at 30±0.05° C. by dissolving the polymer in a solvent mixture composed of 10 parts by weight of phenol and 7 parts by weight of trichlorophenol at a concentration of 0.5 g/dl.

The preferred inherent viscosity of the lactic-acid based polymer is different depending upon the use. For example, an inherent viscosity of 3.0 or more is required for the lactic-acid based polymer, particularly lactic acid homo-polymer, used for internal splint-plates and screws, because they need high strength.

The lactic-acid/glycolic-acid copolymer which is suitable for the matrix of drugs for sustained release contains from 40 to 60% by mole of glycolic acid structure and has an inherent viscosity of preferably from 0.1 to 1.0 dl/g, and more preferably from 0.4 to 0.6 dl/g.

In the latter case, the inherent viscosity $\eta$ of the lactic-acid based polymer is measured with a Ubbelohde viscometer at 25±0.05° C. in a chloroform solution at a concentration of 0.5 g/dl.

In the process of this invention, the term "maintain in a molten state" means that the polymer resulting from polymerization is kept in a molten state at a temperature which is higher than the melting point or the the glass transition point of the polymer, i.e., usually above 50° C., and is high enough to exhibit flowability of the polymer. Consequently, in order to maintain the polymerization product in a molten state in the case where the bioabsorbable polyester is the glycolic-acid based polymer, the treatment is carried out at a temperature of 180° C. or more, i.e., above the melting point of the polymer. For example, the polymer containing 20% by mole of lactic acid structure has a melting point of about 180° C. and polyglycolic acid has a melting point of 230° C.

The upper limit of the treatment temperature may be lower than 300° C., i.e., the heat decomposition temperature of the glycolic-acid based polymer. The temperature is generally 270° C. or less, and preferably 250° C. or less. The most preferred temperature range is from 220° to 240° C. When the bioabsorbable polyester is the lactic-acid based polymer, the treatment temperature may be from 50° to 60° C. or more, i.e., above the glass transition point. In order to obtain the desired polymer within a short time in the presence of a small amount of the catalyst, the treatment temperature is preferably 160° C. or more. However, in the process of this invention, the maintaining the product in the molten state in the second half of polymerization reaction is carried out in the temperature range of from the glass transition point of the resulting polymer to the temperature 200° C. higher than the glass transition point.

The glycolide or lactide used in the process of this invention is a cyclic dimer. The cyclic dimer is readily prepared respectively from glycolic acid or lactic acid by a dehydrating condensation reaction and successive heat decomposition reaction. There are four isomers of lactide, i.e., D-lactide which is the cyclic dimer of D-lactic acid, L-lactide which is the cylic dimer of L-lactic acid, meso-lactide which is the cyclic dimer of D-lactic acid and L-lactic acid, and DL-lactide which is the racemic mixture of D-lactide and L-lactide. Any type of lactide can be used for this invention.

A wide variety of catalysts including known catalysts can be used for the polymerization of glycolide and lactide so long as the catalyst has activity on the polymerization of these compounds. Examplary catalysts suitable for use includes, for example, compounds primarily containing polyvalent metals such as zinc chloride, titanium tetrachloride, iron chloride, boron trifluoride ether complex, aluminum chloride, antimony trifluoride and lead oxide. Particularly tin compounds and zinc compounds are preferred. Stannous octoate is preferably used in particular among the tin compounds.

The preparation process of the bioabsorbable polyester of this invention will be described hereinafter.

In the preparation of the bioabsorbable polyester of this invention, the amount of the above monomers to be used is determined by the proportion of lactic acid structure and glycolic acid structure in the desired bioabsorbable polyester.

Among the bioabsorbable polyester of this invention, the glycolic-acid based polymer having an inherent viscosity of 0.9dl/g is prepared by bulk polymerization in the molten state. A process has also been known which simultaneously uses alcohols and oxy acids such as lauryl alcohol, lactic acid and glycolic acid for the molecular weight regulators and chain extenders.

The polymerization temperature may be in principle higher than the melting point of the monomers, i.e., glycolide and lactide. Temperatures higher than 160° C. are preferred for the preparation of the desired polymer within a short time in the presence of a small amount of the catalyst. However, in the process of this invention, maintaining the product in the molten state is desirably conducted at a temperature of from the melting point of the resulting polymer to 250° C. at least over the second half of the polymerization reaction.

When the temperature is less than the melting point of the resulting polymer, the polymerization system solidifies. Hence, most of unreacted monomers and low molecular weight substances do not evaporate and non-uniformity of reaction conditions also develops due to poor heat transfer and accumulation of heat. Consequently, the resulting polymer tends to cause fluctuations in physical properties and is unsuitable for use in spinning. On the other hand, temperatures exceeding 250° C. lead to unfavorable decomposition of the resulting polymer. A particularly preferred temperature range is from 220° to 240° C.

Further, the process of this invention requires the temperature to be maintained in the above range over the second half of the polymerization period and simultaneously requires maintenance of the interior of the reaction vessel under reduced pressure of 5 mm Hg or less, and preferably 3 mm Hg or less.

Under a pressure higher than 5 mm Hg, unreacted monomers, glycolide in particular, are difficult to remove even though the temperature of the reaction system is maintained in the above specified range.

The process of this invention provides more preferred results by carrying out so-called gas bubbling which passes an inert gas through the reaction mixture in the operation over the second half of the reaction period. The inert gas which may be used includes nitrogen, helium, neon and argon. Nitrogen is preferred.

That is, in the process of this invention, glycolide and/or lactide are polymerized by maintaining the polymerization system in the molten state at temperature above the melting point of the system under reduced pressure. Thereby residual monomers and low molecular weight volatile substances are effectively removed from the polymer and the glycolic-acid based polymer thus obtained is uniform and suitable for use in spinning.

The lactic-acid based polymer in the bioabsorbable polyester of this invention is also prepared by bulk polymerization in the molten state. Similar to the glycolic-acid based polymer, alcohols and oxy acids such as lauryl alcohol, lactic acid and glycolic acid may be added, when necessary, as molecular weight regulators and chain extenders.

The polymerization temperature may be similar to the glycolic-acid based polymer, in principle higher than the melting point of the monomers, i.e., glycolide and lactide. Temperatures higher than 160° C. are preferred for the preparation of the desired polymer within a short time in the presence of a small amount of the catalyst. However, the lactic-acid based polymer is preferably maintained in the molten state in the temperature range of from the glass transition point of the resulting polymer to the temperature 200° C. higher than the glass transition point. The glass-transition points of the lactic-acid/glycolic-acid copolymer and the lactic-acid based polymer are somewhat different depending upon the proportion of glycolic acid structure and lactic acid structure and are about 50° to 60° C.

When the polymerization and treatment temperature is lower than the glass transition temperature of the resulting polymer, the polymerization system becomes very viscous or solidifies. Hence, most of the unreacted monomers and low boiling impurities do not evaporate and it is difficult to decrease the residual amounts of these impurities in the desired polymer. On the other hand, a temperature more than 200° C. above the glass transition point leads to unfavorable decomposition of the resulting polymer. The preferred range of temperature is from 120° to 240° C. Particularly in the case where either D-isomer or L-isomer of lactide is homopolymerized or copolymerized with glycolide in an isomer proportion of 80% or more, the preferred temperature is in the range of from 180° to 240° C.

The lactic-acid based polymer also requires the temperature in the above range to be maintained over the second half of the polymerization reaction and simultaneously requires maintenance of the interior of the reaction vessel under reduced pressure of 5 mm Hg or less, and preferably 3 mm Hg or less.

Under a pressure higher than 5 mm Hg, unreacted monomers, glycolide in particular, are difficult to remove even though the temperature of the treatment is maintained in the above specified range. Consequently a large amount of unreacted monomer remains in the resulting polymer and is liable to cause unfavorable fluctuations in the physical properties, hydrolizability and processability of the polymer.

It is also preferred to carry out gas bubbling similar to the case of the glycolic-acid based polymer by passing an inert gas through the reaction mixture in the operation over the second half of the polymerization reaction. The inert gas which may be used includes nitrogen, helium, neon and argon.

According to information of the present inventors, residual glycolide in the glycolic-acid based polymer is difficult to evaporate and hence a temperature of 180° C. or more is required even under reduced pressure of 5 mm Hg or less in order to effectively eliminate the glycolide. However, in the copolymerization of glycolide and lactide, lactide is thought to be less active in the copolymerization and to remain unreacted in a larger amount during the second half of the polymerization reaction. As a result, it is surprising that unreacted monomers composed of glycolide and lactide can be effectively removed by maintaining the temperature of the copolymer above its glass transition point under reduced pressure of 5 mm Hg or less.

According to the process of this invention, unreacted monomers and volatile impurities are effectively removed from the resulting polymer whereas low molecular weight chain oligomers remain in the polymer. Consequently, the resulting polymer has a wide molecular weight distribution.

In any of the glycolic-acid based polymers and lactic-acid based polymers, the time required for the operation is different depending upon the composition in the copolymerization, molten state temperature and level of pressure reduction. For example, in the case where glycolic acid homopolymer is prepared at a temperature of 220° to 240° C. under reduced pressure of 5 mm Hg or less, the time of approximately 10 to 60 minutes is sufficient. When the molten state temperature is above 240° C., monomer removal efficiency is improved and treatment time can be decreased. However, too high a temperature tends to cause unfavorable decomposition of the polymer. A temperature lower than 220° C. requires a long time for monomer elimination. The treatment time can be further decreased by enhancing pressure reduction and maintaining in a high vacuum.

The present invention will hereinafter be illustrated further in detail by way of examples.

In the examples, properties of the polymers were determined by the following methods.

INHERENT VISCOSITY

A solvent mixture of 10 parts by weight of phenol and 7 parts by weight of trichlorophenol was used for the glycolic-acid based polymer. Chloroform was used for lactic-acid based polymer. In each case, a solution having a concentration of 0.5g/DL was prepared. The time required for flow down of the solution was measured at 30±0.05° C. for glycolic-acid based polymer and 25±0.05 for latic based polymer with a Ubbelohde viscometer. Inherent viscosity was calculated from the following equation:

$$\eta = l_n(t_1/T_0)/c$$

wherein
$T_0$ = reference measuring time
$T_1$ = measuring time of sample
$C$ = concentration of solution (0.5)

COMPOSITION OF COPOLYMER

A 1% hexafluoroisopropanol(HFIP) solution of glycolic-acid based polymer was prepared and a small amount of chloroform deuteride and tetramethylsilane was added to the solution.

A 1% chloroform deuteride solution of lactic-acid based polymer was prepared and a small amount of tetramethylsilane was added to the solution. 'H-NMR spectrum was measured. The mole proportion was calculated from the ratio of peak strengths between methylene hydrogen of glycolic acid structure and methyl hydrogen of lactic acid structure.

AMOUNT OF RESIDUAL MONOMER

Glycolic-acid based polymer was dissolved in hexafluoroisopropanol(HFIP). Lactic-acid based polymer was dissolved in chloroform.

The residual amount was measured by flame ionization detector(FID) gas chromatography at a column temperature of 140° C. with the column of silicon OV-210 having 2 m in length×3 mm in diameter.

TENSILE STRENGTH

Tensile strength at break of a filament was measured with a usual tensile tester using a specimen of 10 cm in length at a crosshead speed of 100 mm/min.

MOLECULAR WEIGHT DISTRIBUTION

The polymer was dissolved in chloroform. The Weight average molecular weight(Mw) and number average molecular weight(Mn) were measured by gel permeation chromatography The molecular weight distribution was evaluated by the ratio Mw/Mn.

EXAMPLE 1

To a thick-walled stainless steel vessel, 2 kg of glycolide having a melting point of from 83.5° to 84.5° C. was charged and a solution of 0.06 g of stannous octoate in 10 ml of toluene and 5.4 g of lauryl alcohol were added to the vessel. The mixture obtained was deaerated for 2 hours in vacuum and then the vessel flooded with nitrogen.

The mixture was heated at 230° to 235° C. for 2 hours with stirring in a nitrogen atmosphere. The polyglycolic acid had an inherent viscosity of 0.91dl/g at that time. Then, keeping the temperature at the same level, pressure reduction was gradually conducted with a vacuum pump through an exhaust tube and a glass receiver. Pressure in the reaction vessel was finally reduced to 3 mm Hg. After an hour from the start of pressure reduction, distillation of monomers and low molecular weight volatile substances ceased. The interior of the vessel was flooded with nitrogen. The resulting polymer was discharged from the bottom of the vessel in the form of string and cut into pellets.

Polyglycolic acid thus obtained was almost colorless and had an inherent viscosity of 1.00 dl/g. The amount of residual monomer was 0.8%.

Melt spinning of the polyglycolic acid pellets was carried out with a usual extruder under an extrusion pressure of 100 kg/cm$^2$ at temperature of 245° C. Spinning was smoothly conducted without end breakage. The string thus obtained was drawn four times at 120° C. to give a good multifilament having a tensile strength of 7.8 g/denier.

EXAMPLE 2

The same polymerization and discharge procedures as described in Example 1 were carried out except that nitrogen gas was bubbled from the lower part of the reactor through a capillary tube into the reaction product in the operation during the second half of the polymerization.

Polyglycolic acid thus obtained was almost colorless and had an inherent viscosity of 1.02 dl/g. The amount of residual monomer was 0.3%.

EXAMPLE 3

Glycolide was polymerized for 2 hours by the same procedures as described in Example 1, and then heated to 240° C. and the pressure in the reaction vessel was reduced to 5 mm Hg at the same time. After an hour, the resultant polymer was pelletized by the same procedures as described in Example 1.

The polyglycolic acid thus Obtained was pale brown colored and had an inherent viscosity of 0.98 dl/g. The amount of residual monomer was 0.9%.

EXAMPLE 4

To a thick-walled stainless steel vessel, 2580 g (22.2 mole) of glycolide having a melting point of 83.5° to 84.5° C. and 420 g (2.9 mole) of L-lactide having a melting point of 97.0° to 98.5° C. were charged. A solution of 0.18 g of stannous octoate in 10ml of toluene and 9.0 g of lauryl alcohol were added to the vessel. The mixture obtained was deaerated for 2 hours in vacuum and then the vessel was flooded with nitrogen. The mixture was heated at 220° C. for 2 hours with stirring in a nitrogen atmosphere. The polymer had an inherent viscosity of 0.90 dl/g at that time. Then keeping the temperature at the same level, pressure reduction is gradually conducted with a vacuum pump through an exhaust tube and a glass receiver. Pressure in the reaction vessel was finally reduced to 3 mm Hg. After an hour from the start of pressure reduction, distillation of monomers and low molecular weight volatile substances was ceased. The interior of the vessel was flooded with nitrogen. The resulting polymer was discharged from bottom of the vessel in the form of string and cut into pellets.

The copolymer obtained was transparent and almost colorless. The copolymer had an inherent viscosity of 0.99 dl/g and contained 11.4% by mole of lactic acid structure. Residual amounts of glycolide and lactide were respectively 0.6% and 0.3%.

Spinning and drawing of the copolymer thus obtained could be smoothly carried out similar to the polymer prepared in Example 1. A good multifilament having a tensile strength of 7.2 g/denier was obtained.

COMPARATIVE EXAMPLE 1 a Polymerization reaction was carried out by the same procedures as described in Example 1 except that the pressure reducing and deairing operation was omitted in the second half of the polymerization and polymerization was conducted for 3 hours. When the polymer was discharged after polymerization from the bottom of the vessel in the form of string, bubbles were generated in the polymer and caused wire breakage. Hence, pelletizing was difficult to carry out and the yield of pellets was lowered about 20%. Polyglycolic acid obtained had an inherent viscosity of 0.93 dl/g. The amount of residual monomer was 6.9%.

Melt spinning of the polymer thus obtained was attempted using the same procedures as described in Example 1. However, bubbles were evolved in the extruded filament and end breakage frequently occurred in the spinning operation. The filament obtained after drawing had a tensile strength of 6.2 g/denier.

COMPARATIVE EXAMPLE 2

A polymerization reaction was carried out by the same procedures as described in Example 1 except that the deairing and pressure reducing operation was conducted while maintaining the temperature at 280° C. in the second half of the polyaerization. The Polyglycolic acid obtained was dark brown colored and had an inherent viscosity of 0.35 dl/g. Thus, the product was unsuitable for spinning.

COMPARATIVE EXAMPLE 3

A polymerization reaction was carried out by the same procedures as described in Example 1 except that the deairing and pressure reducing operation was conducted while maintaining the temperature at 180° C. in the second half of the polymerization.

The reaction product solidified in the second half of the polymerization and hence the reaction product was crushed after finishing the polymerization.

The polyglycolic acid obtained was white colored and the inherent viscosity fluctuated from 0.93 to 0.98 dl/g. The residual amount of the monomer also fluctuated from 2.1 to 5.0%.

Spinning and drawing of the polymer were difficult similar to the polymer of Comparative Example 1.

COMPARATIVE EXAMPLE 4

A polymerization reaction was carried out by the same procedures as described in Example 1 except that the deairing and pressure reducing operation was conducted while maintaining the reduced pressure at 7 mm Hg in the second half of the polymerization. The polyglycolic acid thus obtained contained 2.3% of residual monomer.

EXAMPLE 5

To a cylindrical thick-walled stainless steel polymerization reactor equipped with a stirrer, 2005 g (13.9 mole) of DL-lactide and 2452 g (12.5 mole) of glycolide were charged, and 0.01% by weight of stannous octoate and 0.4% by weight of dl-lactic acid were added to the reactor. The mixture was deaerated for 2 hours in the vacuum of 1 to 5 mm Hg and then the reactor was flooded with nitrogen The mixture was heated at 220° C. for 2 hours with stirring in a nitrogen atmosphere by using a mantle heater. The polymer had an inherent viscosity of 0.45dl/g at that time. Then the temperature was reduced to 160° C., and the reactor was gradually deaerated through an exhaust tube and a glass receiver with a vacuum pump and the pressure in the reactor was finally reduced to 3 mm Hg. After an hour from the start of pressure reduction, distillation of monomers and low molecular weight volatile substances ceased. The interior of the reactor was flooded with nitrogen. The resulting polymer was discharged from bottom of the reactor, guided to a pelletizer and cut into pellets.

The copolymer thus obtained was transparent and almost colorless and an inherent viscosity of 0.51 dl/g. The copolymer had a wide molecular weight distribution of 4.87 and was hence extremely suitable for a matrix for sustained release of drugs. The mole ratio of glycolic acid structure to lactic acid structure was 48/52 in the copolymer. The residual amounts of glycolide and lactide were respectively 0.6% and 0.7%.

EXAMPLE 6

Polymerization and discharge from the reactor were carried out by the same procedures as described in Example 5 except that nitrogen was bubbled from the lower part of the reactor through a capillary tube into the reaction product in the operation over the second half of the polymerization.

The copolymer obtained was transparent and almost colorless and had an inherent viscosity of 0.52 dl/g. The mole ratio of glycolic acid structure to lactic acid structure was 48/52 in the copolymer. The residual amounts of glycolide and lactide were respectively 0.3% and 0.5%.

COMPARATIVE EXAMPLE 5

A polymerization reaction was carried out by the same procedures as described in Example 5 except that the deairing and pressure reducing operation in the second half of the polymerization were omitted and polymerization was conducted for 3 hours.

The copolymer thus obtained was transparent and almost colorless and had an inherent viscosity of 0.49 dl/g.

The mole ratio of glycolic acid structure to lactic acid structure was 47/53 in the copolymer. The residual amounts of glycolide and lactide were respectively 2.1% and 5.1%.

COMPARATIVE EXAMPLE 6

The copolymer obtained in Comparative Example 5 was dissolved in dichloromethane in a concentration of 10% and successively poured into methanol.

Precipitated polymer was recovered by filtration. The filtrate (waste solution) was analyzed by gas chromatography and 'H-NMR spectrum. As a result, low molecular weight copolymer (oligomer) was identified in addition to unreacted monomers such as lactide and glycolide. On the other hand, the recovered copolymer was dried for 24 hours at room temperature under reduced pressure of 3 mm Hg. The dried copolymer was dissolved in hexafluoro-isopropanol and analyzed by gas chromatography. Several percents of dichloromethane and methanol were detected. The copolymer was further dried at 50° C. for 24 hours under reduced pressure. However, from several hundred to several thousand ppm of dichloromethane and methanol still remained in the copolymer. The copolymer thus obtained had a molecular weight distribution of 2.44. The distribution was definitely narrower than that of the copolymer in Example 5.

COMPARATIVE EXAMPLE 7

A polymerization reaction was carried out by the same procedures as described in Example 5 except that the temperature was maintained at 260° C. in the deairing and pressure reducing operation during the second half of the polymerization.

The copolymer thus obtained was deep brown colored and the inherent viscosity decreased to 0.39dl/g.

COMPARATIVE EXAMPLE 8

Polymerization was conducted by the same procedures as described in Example 5 except that the temperature was maintained at 45° C. in the deairing and pressure reducing operation during the second half of the polymerization. The viscosity of reaction mixture was increased in the second half of the polymerization and stirring became impossible. The reaction mixture was crushed after finishing the polymerization reaction.

The copolymer thus obtained was transparent and almost colorless and had an inherent viscosity of 0.46 dl/g.

The mole ratio of glycolic acid structure to lactic acid structure was 47/53 in the copolymer. The residual amounts of glycolide and lactide were respectively 2.6% and 6.3%.

COMPARATIVE EXAMPLE 9

A polymerization reaction was carried out by the same procedures as described in Example 5 except that the reduced pressure was maintained at 7 mm Hg in the deairing and pressure reducing operation during the second half of the polymerization.

The resultant polymer was discharged from the bottom of the reactor in the form of string after finishing the polymerization. In the step, bubbles were generated in the polymer and led to wire breakage. Hence, pelletizing was difficult to carry out.

The residual amounts of glycolide and lactide in the resultant copolymer were respectively 2.4% and 5.5%.

EXAMPLE 7

To a thick-walled cylindrical stainless steel polymerization reactor equipped with a stirrer, 232 g (1.6 mole) of L-lactide and 45 g (0.4 mole) of glycolide were charged, and 0.015% by weight of stannous octoate were added to the reactor. The reactor was then evacuated for 2 hours and flooded with nitrogen.

The mixture obtained was heated at 120° C. for 53 hours with stirring in a nitrogen atmosphere by using an oil bath. The polymer had an inherent viscosity of 2.01 dl/g. Then the temperature was raised to 180° C. and the reactor was gradually deaerated through an exhaust tube and a glass receiver with a vacuum pump and the internal pressure was reduced to 3 mm Hg. At the same time, nitrogen was bubbled from the lower part of the reactor through a capillary tube into the reaction mixture while maintaining the reduced pressure After 2 hours from the start of pressure reduction, distillation of monomers and low molecular weight volatile substances ceased. The interior of the reactor was flooded with nitrogen and the resulting polymer was discharged from the bottom of the reactor in the form of string and cut into pellets.

The copolymer obtained was a white solid and had an inherent viscosity of 2.08 dl/g and a molecular weight distribution of 3.84. The mole ratio of glycolic acid structure to lactic acid structure was 21/79 in the copolymer. The residual amounts of glycolide and lactide were respectively 0.0% and 0.9%.

15

COMPARATIVE EXAMPLE 10

The polymerization reaction was carried out by the same procedures as described in Example 7 except that the pressure reducing and deairing operation was omitted and the polymerization was conducted for 55 hours.

The copolymer thus obtained was a white solid and had an inherent viscosity of 1.62dl/g. The mole ratio of glycolic acid structure to lactic acid structure was 22/78 in the copolymer. The residual amounts of glycolide and lactide were respectively 1.9% and 25.7%.

COMPARATIVE EXAMPLE 11

The copolymer obtained in Comparative Example 10 was subjected to reprecipitation purification by the same procedures as described in Comparative Example 6 and dried at room temperature for 24 hours under reduced pressure of 3 mm Hg. The recovered copolymer contained several percent of the reprecipitation solvent. The molecular weight distribution of the copolymer was 1.75.

EXAMPLE 8

To a thick-walled cylindrical stainless steel polymerization reactor equipped with a stirrer, 216 g (1.5 mole) of L-lactide was charged and 0.003% by weight of stannous octoate and 0.05% by weight of lauryl alcohol were added to the reactor. The reactor was evacuated for 2 hours and flooded with nitrogen.

The mixture thus obtained was heated to 200° C. for 18 hours with stirring in a nitrogen atmosphere by using an oil bath. A polymer had an inherent viscosity of 1.76 dl/g at that time. Maintaining the temperature at the same level, the interior of the reactor was gradually deaerated through an exhaust tube and a glass receiver with a vacuum pump and the pressure reduced to 3 mm Hg. At the same time, nitrogen was bubbled from the lower part of the reactor through a capillary tube into the reaction mixture while maintaining the reduced pressure. After 2 hours from the start of dearing, distillation of monomers and low molecular weight volatile substances ceased. The reactor was flooded with nitrogen and the resulting polymer was discharged from the bottom of the reactor in the form of string and cut into pellets.

The polymer thus obtained was a white solid and had an inherent viscosity of 1.96 dl/g and a molecular weight distribution of 2.37. The amount of residual lactide was 0.7%.

COMPARATIVE EXAMPLE 12

A polymerization was conducted by the same procedures as described in Example 9 except that the pressure reducing and deairing operation was omitted and the polymerization was carried out for 20 hours.

The polymer obtained was a white solid and had an inherent viscosity of 1.67 dl/g. The residual amount of lactide was 17.0%.

COMPARATIVE EXAMPLE 13

The polymer obtained in Comparative Example 12 was subjected to reprecipitation purification by the same procedures as described in Comparative Example 6. The molecular weight distribution of the recover polymer was 2.08.

What is claimed is:

1. A process for the preparation of a bioabsorbable polyester having recurring structural units represented by the formula (I):

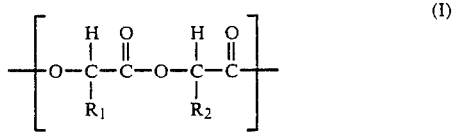

wherein $R_1$ and $R_2$ are a hydrogen atom or a methyl group and can be the same or different, by the polymerization reaction of at least one of a glycolide and a lactide which comprises treating said polyester under reduced pressure in a reaction system while maintaining said polyester in a molten state during the second half of the polymerization reaction.

2. The process of claim 1 wherein the bioabsorbable polyester obtained contains 2% or less of residual monomer.

3. The process of claim 1 wherein the pressure in the reaction system is reduced to about 5 mm Hg or less.

4. The process of claim 1 wherein the pressure in the reaction system is reduced and an inert gas is passed through the polyester in the molten state.

5. The process of claim 1 wherein the pressure in the reaction system is reduced to about 5 mm Hg or less and the inert gas is passed through the polyester in the molten state.

6. The process of claim 1 wherein the bioabsorbable polyester is a glycolic-acid based polymer having recurring units represented by the formula(I) wherein a proportion of from 80 to 100% of $R_1$ and $R_2$ is a hydrogen atom and a proportion of from 0 to 20% of $R_1$ and $R_2$ is a methyl group.

7. The process of claim 6 wherein the bioabsorbable polyester is a a glycolic-acid based polymer having an inherent viscosity of 0.9 dl/g or more.

8. The process of claim 1 wherein the bioabsorbable polyester is a lactic-acid based polymer having recurring units represented by the formula(I) wherein a proportion of from 0 to 80% of $R_1$ and $R_2$ is a hydrogen atom and a proportion of from 20 to 100% of $R_1$ and $R_2$ is a methyl group.

9. The process of claim 8 wherein the bioabsorbable polyester is a lactic-acid based polyester having an inherent viscosity of 0.4 to 0.6 dl/g.

10. The process of claim 6 wherein the temperature in the second half of the reaction is maintained in the range of from the melting point of said polymer to about 250° C.

11. The process of claim 8 wherein the temperature in the second half of the reaction is maintained in the range of from the glass transition point of said polymer to about 200° C. above the glass transition point.

12. A process for the preparation of a bioabsorbable polyester having recurring structural units represented by the formula (I):

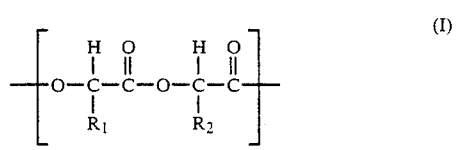

wherein a proportion of from b 80 to 100% of $R_1$ and $R_2$ is a hydrogen atom and a proportion of from 0 to 20% of $R_1$ and $R_2$ is a methyl group, by the polymerization reaction of at least one of a glycolide and a lactide which comprises treating said polyester under reduced pressure of about 5 mm Hg or less in a reaction system while maintaining said polyester in a molten state in the range of from the melting point of said polymer to about 250° C. during the second half of the polymerization reaction.

13. The process of claim 12 wherein an inert gas is passed through the polyester in the molten state.

14. A process for the preparation of a bioabsorbable polyester having recurring structural units represented by the formula (I):

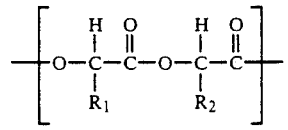

wherein a proportion of from 80 to 100% of $R_1$ and $R_2$ is a hydrogen atom and a proportion of from 20 to 100% of $R_1$ and $R_2$ is a methyl group, by the polymerization reaction of at least one of a glycolide and a lactide which comprises treating said polyester under reduced pressure of about 5 mm Hg or less in a reaction system while maintaining said polyester in a molten stage in the range of from the glass transition point of said polymer to about 200° C. above the glass transition point during the second half of the polymerization reaction.

15. The process of claim 14 wherein an inert gas is passed through the polyester in the molten state.

* * * * *